US011655441B2

(12) United States Patent
Matsumoto (10) Patent No.: US 11,655,441 B2
(45) Date of Patent: May 23, 2023

(54) CELL CULTURE BASE, CELL CULTURE VESSEL, METHOD FOR CULTURING CELLS, METHOD FOR PRODUCING CELLS, METHOD FOR PRODUCING CELL CULTURE BASE, AND METHOD FOR PRODUCING CELL CULTURE VESSEL (71) Applicant: KATAOKA CORPORATION, Kyoto (JP)

(72) Inventor: Junichi Matsumoto, Kyoto (JP)

(73) Assignee: KATAOKA CORPORATION, Kyoto (JP)

( * ) Notice: Subject to any disclaimer, the term of this patent is extended or adjusted under 35 U.S.C. 154(b) by 17 days.

(21) Appl. No.: 16/853,291

(22) Filed: Apr. 20, 2020

(65) Prior Publication Data
US 2020/0339934 A1   Oct. 29, 2020

(30) Foreign Application Priority Data
Apr. 26, 2019  (JP) .............................. JP2019-085165

(51) Int. Cl.
C12M 1/00     (2006.01)
C12M 1/42     (2006.01)
C12M 1/34     (2006.01)
(52) U.S. Cl.
CPC ............ *C12M 31/08* (2013.01); *C12M 21/02* (2013.01); *C12M 35/06* (2013.01); *C12M 41/12* (2013.01)
(58) Field of Classification Search
CPC ...... C12M 31/08; C12M 21/02; C12M 35/06; C12M 41/12

USPC ....................................................... 435/292.1
See application file for complete search history.

(56) References Cited

U.S. PATENT DOCUMENTS

| 5,202,227 | A | 4/1993 | Matsuda et al. |
| 2002/0094572 | A1 | 7/2002 | Singhvi et al. |
| 2003/0148393 | A1 | 8/2003 | Woodbury et al. |
| 2003/0219889 | A1 | 11/2003 | Sumaru et al. |
| 2005/0276456 | A1 | 12/2005 | Yamato et al. |

(Continued)

FOREIGN PATENT DOCUMENTS

| EP | 3 450 471 | 3/2019 |
| JP | 3-007576 | 1/1991 |

(Continued)

OTHER PUBLICATIONS

Kanamori et al., WO2016194454A1 Machine English Translation (Year: 2016).*

(Continued)

*Primary Examiner* — Michael L Hobbs
*Assistant Examiner* — Lenora A Abel
(74) *Attorney, Agent, or Firm* — Hamre, Schumann, Mueller & Larson, P.C.

(57) ABSTRACT

The present invention provides a cell culture base that avoids contact between a photoresponsive layer and cells. The cell culture base of the present invention includes: a support layer; a photoresponsive layer; and a cell culture layer, wherein the photoresponsive layer is laminated on the support layer, the cell culture layer is laminated on the photoresponsive layer, the photoresponsive layer contains a photoresponsive substance that causes at least one of heat and change in magnetism by light irradiation, and the cell culture layer is capable of culturing cells.

16 Claims, 7 Drawing Sheets

(56) References Cited

U.S. PATENT DOCUMENTS

| | | | |
|---|---|---|---|
| 2006/0019390 A1 | 1/2006 | Miyake et al. | |
| 2007/0122901 A1 | 5/2007 | Morita et al. | |
| 2007/0141697 A1 | 6/2007 | Hattori et al. | |
| 2007/0218554 A1* | 9/2007 | Miyake | C12N 5/0068 435/395 |
| 2007/0259328 A1 | 11/2007 | Morita et al. | |
| 2007/0274968 A1 | 11/2007 | Hattori et al. | |
| 2008/0057558 A1 | 3/2008 | Niwa et al. | |
| 2008/0227203 A1* | 9/2008 | Watanabe | C08F 220/56 435/402 |
| 2013/0023025 A1 | 1/2013 | Sumaru et al. | |
| 2013/0045187 A1 | 2/2013 | Semechkin et al. | |
| 2014/0011960 A1 | 1/2014 | Konno et al. | |
| 2014/0099695 A1 | 4/2014 | Furuta et al. | |
| 2015/0044770 A1 | 2/2015 | Kim et al. | |
| 2018/0142193 A1 | 5/2018 | Suzuki et al. | |
| 2018/0319867 A1 | 11/2018 | Koide et al. | |

FOREIGN PATENT DOCUMENTS

| | | | |
|---|---|---|---|
| JP | 2003-009860 | 1/2003 | |
| JP | 2003-088316 | 3/2003 | |
| JP | 2003-339373 | 12/2003 | |
| JP | 4247231 B | 4/2009 | |
| JP | 4303643 B | 7/2009 | |
| JP | 2010-046012 | 3/2010 | |
| JP | 2010-088316 | 4/2010 | |
| JP | 2012-210158 | 11/2012 | |
| JP | 5070565 B | 11/2012 | |
| JP | 5080848 | 11/2012 | |
| JP | 2014-509192 | 4/2014 | |
| JP | 2014-200182 | 10/2014 | |
| JP | 2014-226088 | 12/2014 | |
| JP | 2015195757 A * | 11/2015 | |
| JP | 2017-112923 | 6/2017 | |
| WO | 2004/037968 | 5/2004 | |
| WO | 2005/103227 | 11/2005 | |
| WO | 2011/125615 | 10/2011 | |
| WO | 2012/141202 | 10/2012 | |
| WO | 2015/038011 | 3/2015 | |
| WO | 2016/194454 | 12/2016 | |
| WO | 2016/208673 | 12/2016 | |
| WO | WO-2016194454 A1 * | 12/2016 | C12M 23/20 |
| WO | 2017/213226 | 12/2017 | |

OTHER PUBLICATIONS

Narita, JP2015195757A Machine English Translation (Year: 2015).*
Office Action issued in U.S. Appl. No. 15/576,228 dated Oct. 7, 2019, 11 pages.
Notification of Reasons of Rejection in related Japanese Patent Application No. 2019-176857 dated Nov. 19, 2019, 9 pages with a partial English translation.
Notbohm et al., "Two-Dimensional Culture Systems to Enable Mechanics-Based Assays for Stem Cell-Derived Cardiomyocytes", Experimental Mechanics, 2019, vol. 59, No. 9, pp. 1235-1248.
Intelligent SubstratesTM, BioWriteTM micropatterned substrate specifications, 2010, 1 page.
Intelligent SubstratesTM, BioWriteTM substrate information and protocols, 2010, 2 pages.
Intelligent SubstratesTM, Micropatterned substrates: Highlights from the literature, 2009, 2 pages.
Heinz et al., "Laser inactivation protein patterning of cell culture microenvironments",Lab on a Chip, 2011, vol. 11, pp. 3336-3346.
U.S. Appl. No. 15/576,228, filed Nov. 21, 2017.
Extended European Search Report issued in corresponding European Patent Application No. 19868326.0, dated May 27, 2022, 8 pages.
Notification of Reasons of Rejection in the corresponding Japanese Patent Application No. 2019-085165, dated Jan. 6, 2023, 7 pages with Machine translation.

* cited by examiner

CELL CULTURE BASE, CELL CULTURE VESSEL, METHOD FOR CULTURING CELLS, METHOD FOR PRODUCING CELLS, METHOD FOR PRODUCING CELL CULTURE BASE, AND METHOD FOR PRODUCING CELL CULTURE VESSEL

TECHNICAL FIELD

The present invention relates to a cell culture base, a cell culture vessel, a method for culturing cells, a method for producing cells, a method for producing a cell culture base, and a method for producing a cell culture vessel.

BACKGROUND ART

In recent years, attempts have been made to differentiate target cells, tissues, and the like from pluripotent cells such as induced pluripotent stem cells (iPS cells) and embryonic stem cells (ES cells) and to utilize them for regenerative medicine and drug discovery.

In maintaining the pluripotent cells, some of the proliferated pluripotent cells may differentiate into other cells. In addition, in differentiation from pluripotent cells to target cells or the like, some of the cells may differentiate into non-target cells.

In such a case, removal of cells other than the target cells is currently performed manually. However, this removal operation requires time and labor, for example, being carried out under a microscope, and has a problem that the quality of cells and the like obtained differs greatly depending on the skill level of the operator (Patent Literature 1).

CITATION LIST

Patent Literature

Patent Literature 1: JP 2014-509192 A

SUMMARY OF INVENTION

Therefore, the inventors of the present invention have developed a method of selecting cells by coating a photoresponsive polymer such as a photo-thermal conversion polymer or the like and using a dish formed with a photoresponsive layer. Specifically, first, a photoresponsive layer is formed by coating a photo-thermal conversion polymer onto the surface of the dish. Next, after culturing the cells on the photoresponsive layer of the dish, the photoresponsive layer located directly below the cells to be removed is irradiated with light. As a result, the photo-thermal conversion polymer in the photoresponsive layer converts light into heat, and the cells directly above the site irradiated with light are killed by heat, thereby performing selection of cells.

However, since the photoresponsive layer and the cell are directly or indirectly contacted with each other in the above-described method, if a solvent used in formation of the photoresponsive layer, a side chain (e.g., dye structure described below) that is not bonded to a photo-thermal conversion polymer, or an unpolymerized monomer is eluted, the cells may be affected. In the production of medical cells used in regenerative medicine or the like, cells and solvents are preferably not in contact with each other from the viewpoint of cell quality control.

With the foregoing in mind, it is an object of the present invention to provide a cell culture base that avoids contact between a photoresponsive layer and cells to be avoided.

Solution to Problem

In order to achieve the above object, the present invention provides a cell culture base (hereinafter also referred to as a "culture base") including: a support layer; a photoresponsive layer; and a cell culture layer, wherein the photoresponsive layer is laminated on the support layer, the cell culture layer is laminated on the photoresponsive layer, the photoresponsive layer contains a photoresponsive substance that causes at least one of heat and change in magnetism by light irradiation, and the cell culture layer is capable of culturing cells.

The present invention also provides a cell culture vessel (hereinafter also referred to as "culture vessel") including: the cell culture base according to the present invention.

The present invention also provides a method for culturing cells (hereinafter also referred to as "culture method"), including: a culturing step of culturing cells using the cell culture base according to the present invention.

The present invention also provides a method for producing cells, including: a culturing step of culturing cells using the cell culture base according to the present invention.

The present invention also provides a method for producing a cell culture base (hereinafter also referred to as a "culture base production method"), including: a first laminating step of laminating a photoresponsive layer on a support layer; and a second laminating step of laminating a cell culture layer on the photoresponsive layer, wherein the photoresponsive layer contains a photoresponsive substance that causes at least one of heat and change in magnetism by light irradiation, and the cell culture layer is capable of culturing cells.

The present invention also provides a method for producing a cell culture vessel (hereinafter also referred to as a "culture vessel production method"), including: a first laminating step of laminating a photoresponsive layer on a support layer; a second laminating step of laminating a cell culture layer on the photoresponsive layer; and a forming step of forming a vessel including the support layer, the photoresponsive layer, and the cell culture layer, wherein the photoresponsive layer contains a photoresponsive substance that causes at least one of heat and change in magnetism by light irradiation, and the cell culture layer is capable of culturing cells.

Advantageous Effects of Invention

The cell culture base of the present invention avoids contact between a photoresponsive layer and cells.

BRIEF DESCRIPTION OF DRAWINGS

FIGS. 5A to 5D are schematic views showing an exemplary culture vessel of the third embodiment. FIG. 5C is a schematic cross-sectional view taken along the line II-II in FIG. 5C.

DESCRIPTION OF EMBODIMENTS

In the present invention, a "cell" refers to, for example, an isolated cell, a cell mass composed of cells, a tissue, or an organ. The cell may be, for example, a cultured cell or a cell isolated from a living body. The cell mass, the tissue, or the organ may be, for example, a cell mass, a cell sheet, a tissue, or an organ produced from the cells, or may be a cell mass, a tissue, or an organ isolated from a living body.

The present invention is described in detail below with reference to the drawings. It is to be noted, however, that the present invention is by no means limited or restricted by the following description. Note that the same reference signs may be given to the same components in FIGS. 1 to 7 below and descriptions thereof may be omitted. Furthermore, for convenience in explanation, the structure of each component shown in the drawings may be appropriately simplified, and the size, the ratio, and the like of components may be schematically shown and different from actual ones. Regarding the descriptions of the embodiments, reference can be made to each other unless otherwise stated.

<Cell Culture Base>

As described above, the cell culture base of the present invention includes: a support layer; a photoresponsive layer; and a cell culture layer, wherein the photoresponsive layer is laminated on the support layer, the cell culture layer is laminated on the photoresponsive layer, the photoresponsive layer contains a photoresponsive substance that causes at least one of heat and change in magnetism by light irradiation, and the cell culture layer is capable of culturing cells. The culture base of the present invention is characterized in that a cell culture layer capable of culturing cells is laminated on the photoresponsive layer, and other configurations and conditions are not particularly limited. In the culture base of the present invention, since the cell culture layer is laminated on the photoresponsive layer, the cell culture layer is interposed between the cells cultured on the cell culture layer and the photoresponsive layer. Thus, the culture base of the present invention avoids contact between the photoresponsive layer and the cells. Accordingly, for example, the influence on the cells of the solvent used in formation of the photoresponsive layer, a side chain (e.g., dye structure described below) that is not bonded to the photo-thermal conversion polymer, or an unpolymerized monomer can be prevented.

First Embodiment

Figure 1:
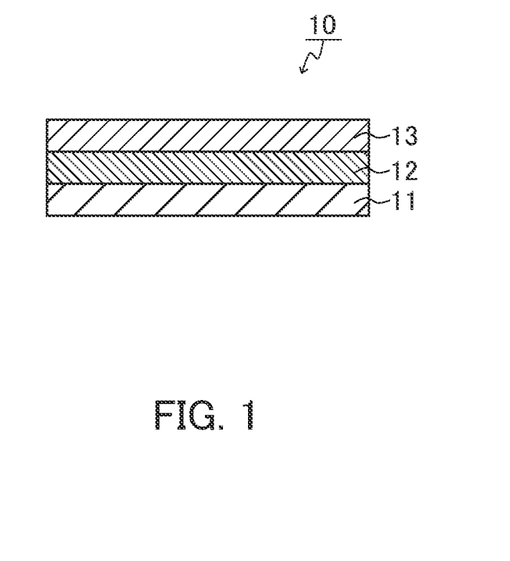
FIG. 1 is a schematic cross-sectional view showing an exemplary configuration of a culture base according to the first embodiment.

The present embodiment relates to an exemplary cell culture base. FIG. 1 is a schematic cross-sectional view showing the configuration of a culture base 10 according to the first embodiment. As shown in FIG. 1, the culture base 10 includes a support layer 11, a photoresponsive layer 12, and a cell culture layer 13. The photoresponsive layer 12 is laminated on the support layer 11, and the cell culture layer 13 is laminated on the photoresponsive layer 12. In other words, in the culture base 10, the support layer 11, the photoresponsive layer 12, and the cell culture layer 13 are laminated (placed) in this order from the bottom surface.

The support layer 11 is a layer serving as a scaffold for forming the photoresponsive layer 12, and can be referred to as, for example, a base or a base layer. The support layer 11 may be any support capable of forming the photoresponsive layer 12 described below, and may be, for example, a sheet-like or plate-like support. Specific examples of the support layer 11 include a film, a thin film, or a plate made of a resin such as a polystyrene-based polymer such as polystyrene; polyethylene terephthalate (PET); a polyimide-based polymer such as polyimide; a polycarbonate-based polymer such as polycarbonate; and a polyolefin-based polymer such as polyolefin; and a sheet glass or film glass such as a glass substrate. As the support made of glass, a slide glass, a preparation, or the like may be used.

The photoresponsive layer 12 is a layer containing a photoresponsive substance (photoresponsive molecule) that causes at least one of heat and change in magnetism by light irradiation. The photoresponsive layer 12 may cause only heat or change in magnetism by light irradiation or may cause both heat and change in magnetism, for example. When the photoresponsive layer 12 causes heat and change in magnetism by light irradiation, the photoresponsive layer 12 may include for example, a layer that causes heat by light irradiation and a layer that causes change in magnetism as separate layers or as one layer. The magnetism can also be referred to as a magnetic property, for example.

If the photoresponsive layer 12 contains a photoresponsive substance that causes heat by light irradiation, the photoresponsive layer 12 can also be referred to, for example, as a photo-thermal conversion layer. The expression "causes heat by light irradiation" means, for example, that the temperature change is significantly increased as compared to the temperature change (increasing temperature) before and after irradiation of a site of a control culture base irradiated with light, i.e., the temperature is increased. The control culture base to be irradiated with light is, for example, a culture base having the same configuration as the culture base of the present invention except that it does not include the photoresponsive layer 12.

When the photoresponsive layer 12 is the photo-thermal conversion layer, the photoresponsive layer 12 contains, as the photoresponsive substance, a molecule (a photo-thermal conversion molecule) capable of converting light into heat. Preferably, the photo-thermal conversion molecule is easily coated onto the support layer 11. The photo-thermal conversion molecule is preferably formed of a polymer containing a dye structure (chromophore) that absorbs light L at a wavelength for irradiation in the culture method described below. The polymer contains, for example, a main chain and a side chain, and preferably has a dye structure in the side chain. The main chain is not particularly limited, and any polymer skeleton can be used. Examples of the polymer skeleton include an acrylic polymer, a polystyrene polymer, a polyolefin polymer, polyvinyl acetate, polyvinyl chloride, a polyolefin polymer, a polycarbonate polymer, and an epoxy polymer. Examples of the dye structure that absorbs light L include derivatives of organic compounds such as azobenzene, diarylethene, spiropyran, spirooxazine, flugide, a leuco dye, indigo, carotenoid (carotene, etc.), flavonoid (anthocyanin, etc.), and quinoid (anthraquinone, etc.). As a specific example, the photo-thermal conversion molecule can be, for example, poly[methylmethacrylate-co-(disperse yellow-7-methacrylate)] $((C_5H_8O_2)_m(C_{23}H_{20}N_4O_2)_n)$ represented by the following formula (1). In the following formula (1), as the structure of azobenzene in the polymer, any of various structures modified with a nitro group, an amino group, a methyl group, or the like may be adopted in addition to unsubstituted azobenzene. In the following formula (1), m and n are represented by percentages by mole. The sum of m and n is, for example, 100 mol %. The photoresponsive layer 12 may contain one kind of photo-thermal conversion molecule or a plurality of kinds of photo-thermal conversion molecules, for example.

(1)

The photo-thermal conversion molecule may be a nanocarbon. Examples of the nanocarbon include a carbon nanotube, graphene, and carbon black, and a carbon nanotube is preferable because of its high photo-thermal conversion efficiency. The carbon nanotube may be a single-walled nanotube (SWNT) or a multi-walled nanotube (MWNT).

When the photoresponsive layer 12 contains a photoresponsive substance that causes change in magnetism by light irradiation, the photoresponsive layer 12 can also be referred to as a photo-magnetism conversion layer, for example. The expression "causes change in magnetism by light irradiation" means that the magnetism of a site to be irradiated with light is significantly changed by, for example, light irradiation. The change in magnetism may be, for example, an increase or decrease in magnetic property or a loss of magnetic property.

When the photoresponsive layer 12 is the photo-magnetism conversion layer, the photoresponsive layer 12 contains, as the photoresponsive substance, a molecule (photo-magnetism conversion molecule) capable of converting light into change in magnetism. As the photo-magnetism conversion molecule, a magnetic substance, which is used for a recording layer of a magneto optical disk and causes change in magnetism by light irradiation, can be used. Specific examples of the photo-magnetism conversion molecule include an alloy of a rare earth and a transition metal such as Tb(terbium)Fe(iron), TbFeCo(cobalt), TbCo, Gd(gadolinium)FeCo, Dy(dysprosium)TbFeCo, or the like; an Mn-based alloy such as Mn(manganese)Bi(bismuth), MnCu(copper)Bi, or the like; and a platinum alloy such as Pt(platinum)/Co, or the like.

While the culture base 10 of the first embodiment includes a single photoresponsive layer 12, the culture base 10 may include a plurality of photoresponsive layers 12. In this case, the photoresponsive layers 12 are preferably placed between the support layer 11 and the cell culture layer 13. While the photoresponsive layer 12 is placed so as to be in contact with the cell culture layer 13 in the culture base 10 of the first embodiment, the photoresponsive layer 12 may be placed so as not to be in contact with the cell culture layer 13. In this case, the photoresponsive layer 12 and the cell culture layer 13 may be thermally or magnetically connected to each other. Specifically, a heat conductive layer for conducting heat caused in the photoresponsive layer 12 to the cell culture layer 13 or a magnetic conductive layer for conducting a change in magnetism caused in the photoresponsive layer 12 to the cell culture layer 13 is formed between the photoresponsive layer 12 and the cell culture layer 13. The heat conductive layer or the magnetic conductive layer contains a molecule having high thermal conductivity or magnetic conductivity, such as a metal, for example.

The cell culture layer 13 is a layer capable of culturing cells. The cell culture layer 13 can also be referred to as a layer that forms the bottom surface of a space (cell culture area) in which cells can be cultured, for example. The cell culture layer 13 can also be referred to as a blocking layer, a shielding layer, or an isolating layer because it can block or shield the cells from contacting the photoresponsive layer 12. The cells are cultured on the upper surface of the cell culture layer 13, i.e. in a space above the surface of the cell culture layer 13 facing away from the photoresponsive layer 12. In culturing the cells, the cells may or may not be in contact with the cell culture layer 13, for example.

The cell culture layer 13 can be formed of, for example, the same material as the material for forming the bottom surface in the cell culture vessel. As a specific example, the cell culture layer 13 can be formed of, for example, a polystyrene-based polymer such as polystyrene; polymethylpentene; a polycarbonate-based polymer such as polycarbonate; PET; a polypropylene-based polymer such as polypropylene; cycloolefin polymer; a polyimide-based polymer such as polyimide; glass; quartz; a silicone resin; a cellulose-based material; or the like. The cell culture layer 13 is not formed of an extracellular matrix, for example.

The surface of the cell culture layer 13 may be treated to improve the adhesion of cells, for example. The treatment can be, for example, a treatment for hydrophilizing the surface of the cell culture layer 13 on the cell culture area side. As a specific example, the treatment can be, for example, a plasma treatment or the like.

In the culture base 10 of the first embodiment, the thicknesses of the support layer 11, the photoresponsive layer 12, and the cell culture layer 13 are not particularly limited. The thickness of the support layer 11 is, for example, 1 μm to 5000 μm. The thickness of the photoresponsive layer 12 is, for example, 1 nm to 5 μm. The thickness of the cell culture layer 13 is, for example, 1 nm to 5 μm. The thickness of the cell culture layer 13 is preferably adjusted so that the heat or change in magnetism caused in the photoresponsive layer 12 can be transferred to the cells of the cell culture layer 13.

Next, an example of the method for producing the culture base 10 of the first embodiment will be described.

In the method for producing the culture base 10, first, the photoresponsive layer 12 is laminated on the support layer 11 (first laminating step). In the first laminating step, the method for laminating the photoresponsive layer 12 is not particularly limited, and can be performed by a general film forming method, and specific examples of the method include a coating method such as coater type, a die type, a doctor blade type, or the like; a printing method (screen method); a vapor deposition method; a sputtering method, a casting method, and a spin coating method.

When the photoresponsive layer 12 is the photo-thermal conversion layer, that is, when the photoresponsive layer 12 contains a photo-thermal conversion polymer that causes heat by light irradiation, the photoresponsive layer 12 is laminated using the photo-thermal conversion polymer in the first laminating step. Specifically, in the first laminating step, the photoresponsive layer 12 may be formed by performing the above-described film forming method such as a coating method, a printing method, a casting method, a spin coating method, or the like using the photo-thermal conversion polymer, or the photoresponsive layer 12 may be formed by performing the above-described film forming method such as a coating method, a printing method, a casting method, a spin coating method, or the like using a solvent containing monomers of the photo-thermal conversion polymer and a polymerization initiator. In the first laminating step, the photoresponsive layer 12 may be formed as a film in advance, and the obtained film-like photoresponsive layer 12 may be laminated on the support layer 11. The solvent can be appropriately determined depending on the type of the monomer and the polymerization initiator, and an organic solvent is given as a specific example.

When the photoresponsive layer 12 is the photo-magnetism conversion layer, that is, when the photoresponsive layer 12 contains a magnetic substance that causes change in magnetism by light irradiation, the photoresponsive layer 12 is laminated using the magnetic substance in the first laminating step. Specifically, in the first laminating step, the photoresponsive layer 12 may be formed by performing the above-described film forming method such as a vapor deposition method, a sputtering method, or the like using the magnetic substance. Alternatively, the photoresponsive layer 12 may be formed by performing the above-described film forming method such as a coating method, a printing method, a casting method, a spin coating method, or the like using a solvent containing the magnetic substance and the polymer. In the first laminating step, the photoresponsive layer 12 may be formed as a film or a plate (board) in advance, and the obtained film or plate-like photoresponsive layer 12 may be laminated on the support layer 11.

Next, in the method for producing the culture base 10, the cell culture layer 13 is laminated on the photoresponsive layer 12 (second laminating step). In the second laminating step, the method for laminating the cell culture layer 13 is not particularly limited, and can be performed by a general film forming method, and specific examples of the method include a coating method, a printing method (screen method), a vapor deposition method, a sputtering method, a casting method, and a spin coating method. Specifically, in the second laminating step, the cell culture layer 13 may be formed by performing the above-described film forming method such as a coating method, a printing method, a casting method, a spin coating method, or the like using a solvent containing a plastic or a glass constituting the cell culture layer 13. In the second laminating step, the cell culture layer 13 may be formed as a film or a plate (board) in advance, and the obtained film or plate-like cell culture layer 13 may be laminated on the photoresponsive layer 12. In this manner, the culture base 10 can be produced.

Figure 2A:
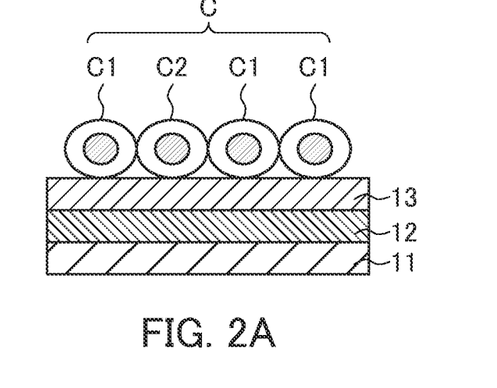
FIGS. 2A to 2C are schematic views showing an example of the method for culturing cells using the culture base of the first embodiment.
Figure 2B:
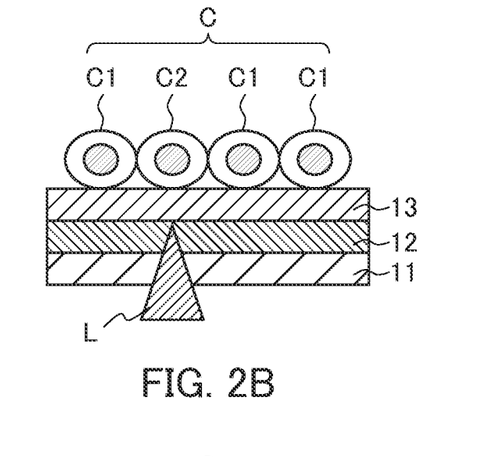
Figure 2C:
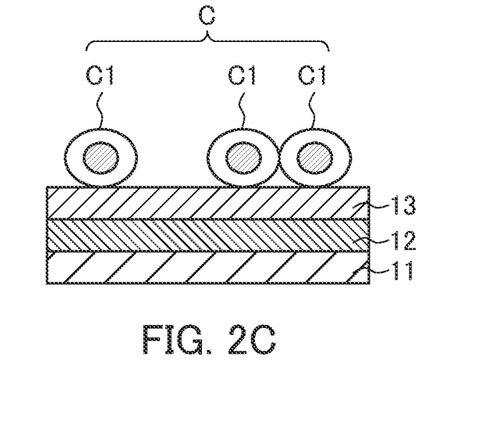

Next, an example of the method for culturing cells using the culture base 10 of the first embodiment will be described with reference to FIGS. 2A to 2C. FIGS. 2A to 2C are schematic views showing an example of the method for culturing and selecting cells using the culture base 10 in which the photoresponsive layer 12 contains a photo-thermal conversion polymer.

First, as shown in FIG. 2A, in the method for culturing cells of the first embodiment, cells C are cultured using the culture base 10 (culturing step). Specifically, the cells C are seeded on the culture base 10, and the cells C are cultured on the cell culture layer 13 of the culture base 10. The cells C include cells C1 to be selected (desired cells) and a cell C2 not to be selected. The culture medium used in the culturing step can be appropriately determined depending on the type of the cell C. The culturing conditions in the culturing step can be appropriately determined depending on the type of the cell C.

Next, cells C1 to be selected are selected from the cells C (selecting step). Specifically, as shown in FIG. 2B, the photoresponsive layer 12 of the culture base 10 located directly below the cell C2 not to be selected is irradiated with light L. The light L is preferably laser light. The spot diameter of the light L is, for example, 10 to 200 µm. The wavelength of the light L can be appropriately set in accordance with the wavelength absorbed by the photo-thermal conversion polymer. When the photo-thermal conversion polymer is a polymer of the formula (1), the wavelength of the light L is, for example, about 405 nm. The amount of energy of the light L is preferably an amount of energy that allows a temperature at which the cells laminated on the cell culture layer 13 are killed. Specifically, the amount of energy of the light L is, for example, an amount of energy that allows the temperature of the cell culture layer 13 directly above a site of the photoresponsive layer 12 irradiated with the light L to be 50° C. or more, 60° C. or more, 70° C. or more, 80° C. or more, or 90° C. or more, preferably 100° C. or more, 110° C. or more, or 120° C. or more. As a result, as shown in FIG. 2C, the cell C2 is removed by being killed by heat, and the cells C1 to be selected can be selected. While the present embodiment is described with reference to an example in which the photoresponsive layer 12 contains a photo-thermal conversion polymer as the photo-thermal conversion molecule, the photo-thermal conversion molecule may be a nanocarbon. When the photo-thermal conversion molecule is a nanocarbon, the wavelength of the light L is, for example, a wavelength within the near-infrared region.

Figure 3A:
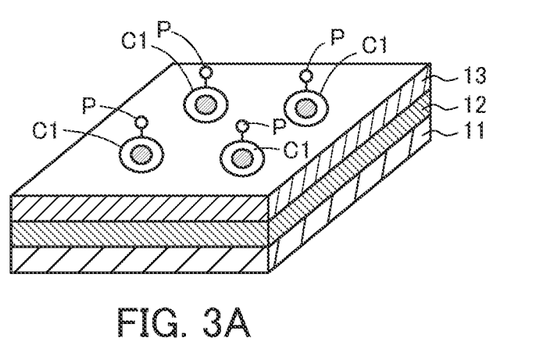
FIGS. 3A to 3C are schematic views showing an example of the method for culturing cells using the culture base of the first embodiment.
Figure 3B:
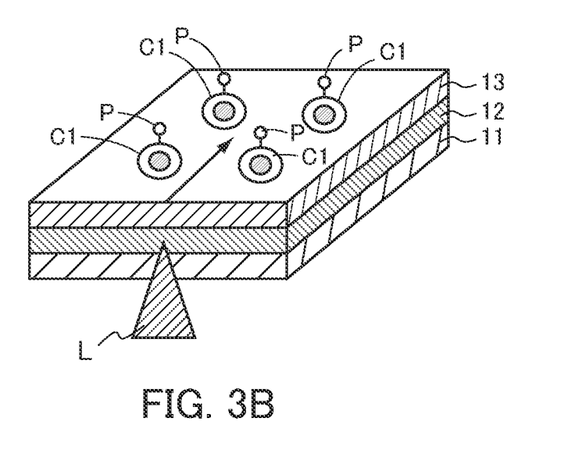
Figure 3C:
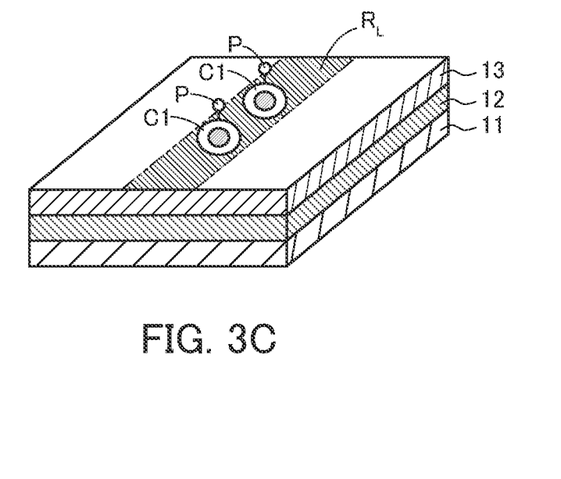

Next, an example of the method for culturing cells using the culture base 10 of the first embodiment will be described with reference to FIGS. 3A to 3C. FIGS. 3A to 3C are schematic views showing an example of the method for culturing and placing cells using the culture base 10 in which the photoresponsive layer 12 contains a magnetic substance.

First, as shown in FIG. 3A, in the method for culturing cells of the first embodiment, cells C are cultured using the culture base 10 (culturing step). Specifically, the cells C are seeded on the culture base 10, and the cells C are cultured on the cell culture layer 13 of the culture base 10. The cell C is labeled with a magnetic substance P. The magnetic substance P can be, for example, a magnetic bead or the like.

Next, the cells C are placed at desired positions. Specifically, the photoresponsive layer 12 of the culture base 10 located directly below the area where the cells C are placed is irradiated with light L. Since the cells C are placed linearly in the present embodiment, the photoresponsive layer 12 is linearly irradiated with the light L as indicated by the arrow in FIG. 3B. In addition to the irradiation of the light L, a magnetic force is applied to an area of the photoresponsive layer 12 to be irradiated by using a magnet or the like so as to impart a magnetic force to attract the magnetic substance P. The magnetic substance included in the photoresponsive layer 12 is such that the coercive force of the magnetic substance is lost (loss of magnetism) when it reaches the Curie temperature by light, and the magnetic substance retains (memorizes) the applied magnetic force by applying a magnetic force at the instant when the temperature of the magnetic substance drops from the Curie temperature. Therefore, when the photoresponsive layer 12 is a photo-magnetism conversion layer, a magnetic force for attracting the magnetic substance P to a desired area $R_L$ can be imparted by being irradiated with the light L. As a result, as shown in FIG. 3C, the magnetic substance P labeling the cells C is attracted to the desired region $R_L$, and the cells C can be arranged (linearly in FIG. 3C) in the desired region $R_L$.

In the culture base 10 of the first embodiment, since the cell culture layer 13 is laminated on the photoresponsive layer 12, the cell culture layer 13 is interposed between the cells C cultured on the cell culture layer 13 and the photoresponsive layer 12. Thus, the culture base 10 of the first embodiment avoids contact between the photoresponsive layer 12 and the cells C. Accordingly, for example, the influence on the cells of the solvent used in formation of the photoresponsive layer 12, a side chain (e.g., the dye structure mentioned above) that is not bonded to the photo-thermal conversion polymer, or an unpolymerized monomer can be prevented.

Second Embodiment

Figure 4:
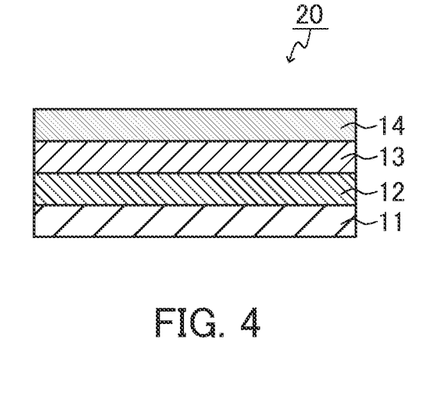
FIG. 4 is a schematic cross-sectional view showing an exemplary culture base according to the second embodiment.

The present embodiment relates to another example of the cell culture base. FIG. 4 is a schematic cross-sectional view showing the configuration of a culture base 20 according to the second embodiment. As shown in FIG. 4, the culture base 20 includes a scaffold base layer 14 in addition to the layers of the culture base 10 of the first embodiment. The scaffold base layer 14 is laminated on the cell culture layer 13. In the culture base 20, the support layer 11, the photoresponsive layer 12, the cell culture layer 13, and the scaffold base layer 14 are laminated in this order from the bottom surface. Except for this point, the culture base 20 of the second embodiment has the same configuration as that of the culture base 10 of the first embodiment, and reference can be made to the description of the first embodiment.

The scaffold base layer 14 is a layer containing a scaffold base. The scaffold base means, for example, a substance that serves as a scaffold for cells when cells are cultured. The scaffold base may be, for example, an extracellular substance (extracellular matrix) or a substance having a function as a scaffold of cells. Examples of the extracellular matrix include elastin; entactin; collagens such as type I collagen, type II collagen, type III collagen, type IV collagen, type V collagen, and type VII collagen; tenascin; fibrillin; fibronectin; laminin; vitronectin; proteoglycan composed of sulfated glycosaminoglycans such as chondroitin sulfate, heparan sulfate, keratan sulfate, and dermatan sulfate and core proteins; glucosaminoglycans such as chondroitin sulfate, heparan sulfate, keratan sulfate, dermatan sulfate, and hyaluronic acid; Synthemax® (vitronectin derivative); and Matrigel® (mixtures of laminin, type IV collagen, heparin sulfate proteoglycan, and entactin/nidogen). The extracellular matrix is preferably laminin. The scaffold base may contain a peptide fragment of the protein or a fragment of the sugar chain. As a specific example, the peptide fragment of the protein can be, for example, a fragment of laminin. Examples of the fragment of laminin include laminin 211-E8, laminin 311-E8, laminin 411-E8, and laminin 511-E8. The laminin 211-E8 is composed of fragments of the α2 chain, β1 chain, and γ1 chain of laminin. The laminin 311-E8 is composed of fragments of the α3 chain, β1 chain, and γ1 chain of laminin. The laminin 411-E8 is composed of fragments of the α4 chain, β1 chain, and γ1 chain of laminin. The laminin 511-E8 is composed of, for example, fragments of the α5 chain, β1 chain, and γ1 chain of laminin.

While the culture base 20 of the second embodiment includes a single scaffold base layer 14, the culture base 20 may include a plurality of scaffold base layers 14.

The scaffold base layers 14 may further contain other components in addition to the scaffold base. Examples of the other components include buffers, salts, growth factors (cell growth factors), cytokines, and hormones.

Next, an example of the method for producing the culture base 20 of the second embodiment will be described. The method for producing the culture base 20 of the second embodiment includes a third laminating step of laminating the scaffold base layer 14 on the cell culture layer 13 in addition to the steps of the method for producing the culture base 10 of the first embodiment. Except for this point, the method for producing the culture base 20 of the second embodiment is the same as that of the culture base 10 of the first embodiment, and reference can be made to the description of the first embodiment.

In the third laminating step, the scaffold base layer 14 is laminated using a scaffold base. In the third laminating step, the method for laminating the scaffold base layer 14 is not particularly limited, and can be performed using a solution containing the scaffold base by a general film forming method, and specific examples of the method include a coating method, a printing method (screen method), a vapor deposition method, a sputtering method, a casting method, and a spin coating method.

The method for culturing cells using the culture base 20 of the present embodiment can be performed, for example, in the same manner as the method using the culture base 10 of the first embodiment described above.

Since the culture base 20 of the second embodiment includes the scaffold base layer 14, cells can be cultured in suitable environments.

<Cell Culture Vessel>

The cell culture vessel of the present invention includes the cell culture base of the present invention as described above. The culture vessel of the present invention is characterized in that it includes the culture base of the present invention, and other configurations and conditions are not particularly limited. In the culture vessel of the present invention, since the cell culture layer is laminated on the photoresponsive layer, the cell culture layer is interposed between the cells cultured on the cell culture layer and the photoresponsive layer. Thus, the culture vessel of the present invention avoids contact between the photoresponsive layer and the cells. Accordingly, for example, the influence on the cells of the solvent used in formation of the photoresponsive layer, a side chain (e.g., the dye structure mentioned above) that is not bonded to the photo-thermal conversion polymer, or an unpolymerized monomer can be prevented. Further, since the culture vessel of the present invention can be produced by using the culture base of the present invention as described below, for example, the shape of the culture vessel can be any shape. Regarding the culture vessel of the present invention, reference can be made to the description as to the culture base of the present invention.

Third Embodiment

Figure 5A:
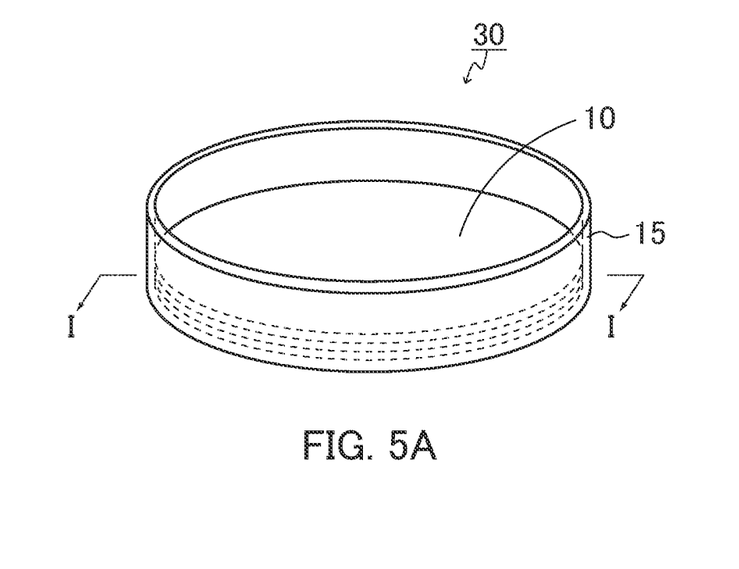
FIG. 5A is a schematic perspective view of the culture vessel.
Figure 5B:
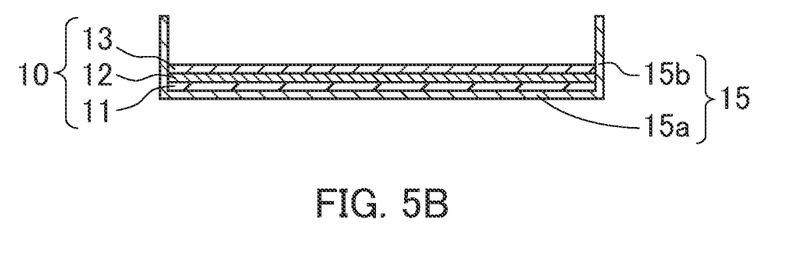
FIG. 5B is a schematic cross-sectional view taken along the line I-I in FIG. 5A.

The present embodiment relates to an exemplary cell culture vessel. FIGS. 5A and 5B are schematic views showing the configuration of the culture vessel 30 according to the third embodiment. FIG. 5A is a schematic perspective view of the culture vessel 30. FIG. 5B is a schematic cross-sectional view taken along the line I-I in FIG. 5A. As shown in FIG. 5A, the culture vessel 30 includes a vessel 15 and a culture base 10. The vessel 15 includes a bottom surface 15a and a side wall 15b. As shown in FIG. 5B, the culture base 10 is placed such that its bottom surface (the bottom surface of a support layer 11) is brought into contact with the upper surface of the bottom surface 15a. That is, in the culture vessel 30, the bottom surface 15a, the support layer 11, the photoresponsive layer 12, and the cell culture layer 13 are laminated (placed) in this order from the bottom surface. The configuration of the culture base 10 is the same as that of the culture base 10 of the first embodiment, and reference can be made to the description of the first embodiment.

In the vessel 15, the cells can be cultured. In the vessel 15, a space surrounded by the cell culture layer 13 of the culture base 10 placed on the bottom surface 15a and the side wall 15b is an area where the cells can be cultured (cell culture area). The vessel 15 can be a cell culture vessel, and specific examples thereof includes a dish, a plate, a flask (cell culture flask), and the like. The size, volume, material, whether or not the adhesive treatment has been performed, and the like of the vessel 15 can be appropriately determined in accordance with the type and amount of the cells to be cultured in the culture vessel 30.

The vessel 15 has one cell culture area but may have a plurality of cell culture areas. In the latter case, the vessel 15 can also be said to have wells, for example. In the latter case, the culture base 10 may be placed in any one of or some of the cell culture areas, or the culture bases 10 may be placed in all of the cell culture areas. That is, in the vessel 15, the culture base 10 may be placed in any one or more of wells or all of wells.

In the present embodiment, the vessel 15 may include a lid. The lid may detachably cover, for example, the top surface of the vessel 15. The lid is placed so as to face the bottom surface 15a, for example. The lid may be, for example, a lid of the cell culture vessel.

Figure 5C:
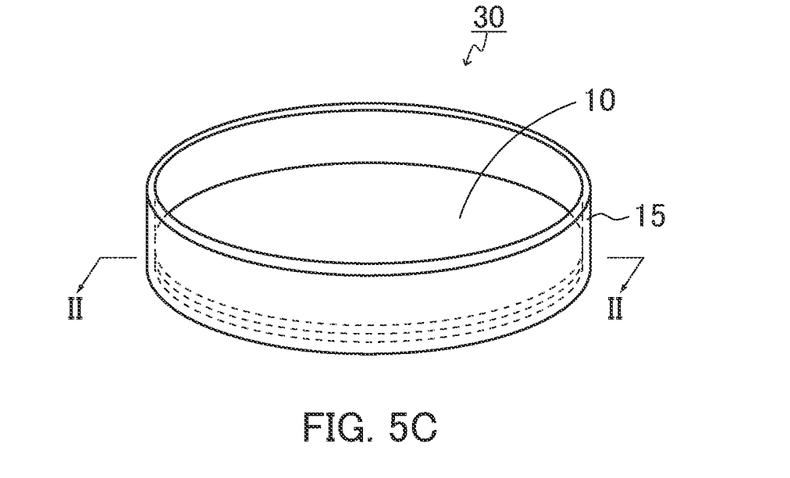
FIG. 5C is a schematic perspective view of the culture vessel.
Figure 5D:
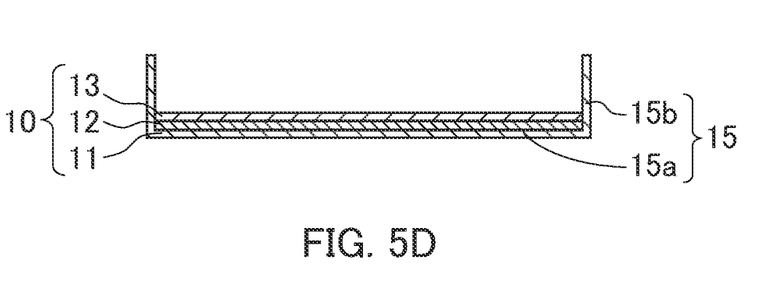
FIG. 5D is a schematic perspective view of the culture vessel.

While the culture base 10 is laminated on the bottom surface 15a of the vessel 15 in the culture vessel 30 of the present embodiment, the placement of the culture base 10 is not limited thereto. The culture base 10 may be placed on the inner peripheral surface of the side wall 15b, i.e., on the cell culture area side, in addition to or instead of the bottom surface 15a of the vessel 15, for example. The culture base 10 is placed on the inner peripheral surface of the side wall 15b such that the cell culture layer 13 is placed on the cell culture area side. In the present embodiment, the culture base 10 is placed on the bottom surface 15a of the vessel 15, and the support layer 11 in the culture base 10 and the bottom surface 15a are formed as independent components. The present invention, however, is not limited thereto. For example, as shown in FIGS. 5C and 5D, the bottom surface 15a may constitute the support layer 11. That is, in the culture vessel of the present invention, the bottom surface 15a and the support layer 11 may be formed as a single member. In this case, in the method for producing the culture vessel of the present invention described below, the culture vessel 30 is produced using the bottom surface 15a serving as the support layer 11 and laminating the photoresponsive layer 12 and the cell culture layer 13 thereon.

The culture vessel 30 may further include the scaffold base layer described above. That is, the culture vessel 30 may include the culture base 20 instead of the culture base 10.

Next, an example of the method for producing the culture vessel 30 according to the third embodiment will be described with reference to FIGS. 6A to 6C.

Figure 6A:
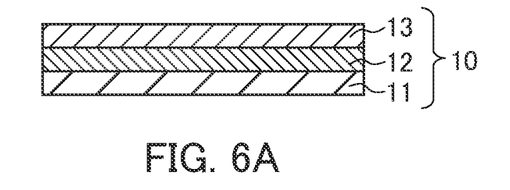
FIGS. 6A to 6C are schematic views showing an example of the method for producing a culture vessel according to the third embodiment.

In the method for producing the culture vessel 30 of the present embodiment, first, as shown in FIG. 6A, the culture base 10 is produced. Specifically, in the method for producing the culture vessel 30, the photoresponsive layer 12 is laminated on the support layer 11 (first laminating step). Next, the cell culture layer 13 is laminated on the photoresponsive layer 12 (second laminating step). The first laminating step and the second laminating step are the same as those in the method for producing the culture base 10 of the first embodiment, and reference can be made to the description of the first embodiment.

Figure 6B:
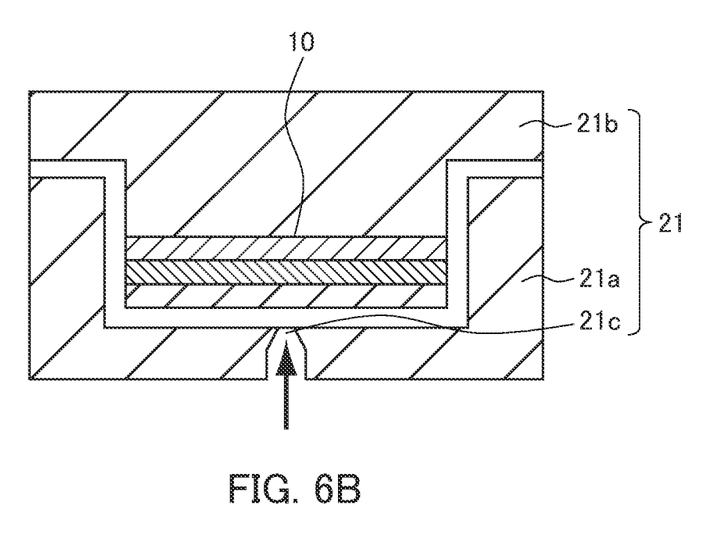
Figure 6C:
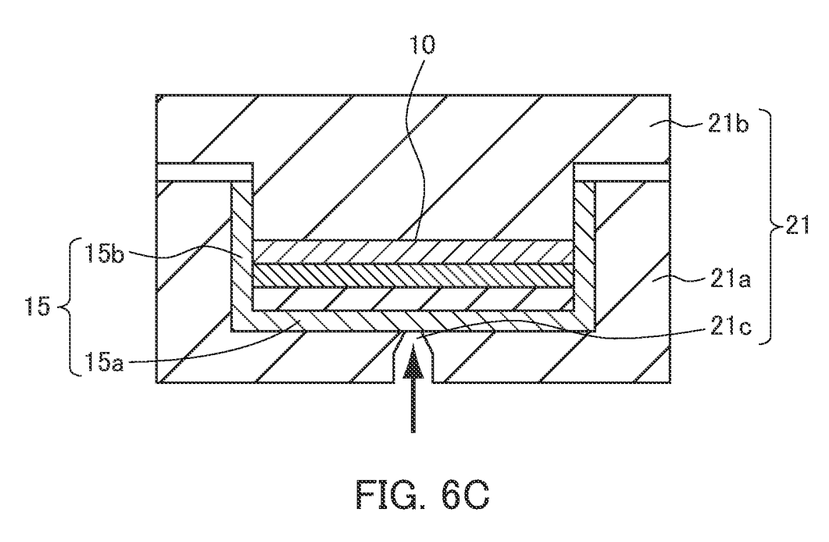

Next, as shown in FIGS. 6B and 6C, the vessel 15 including the support layer 11, the photoresponsive layer 12, and the cell culture layer 13 is formed (vessel forming step). Specifically, a die 21 capable of forming the vessel 15 is prepared. The die 21 is composed of a die 21a (fixed side template) and a die 21b (working side template). As shown in FIG. 6B, the culture base 10 is placed such that the cell culture layer 13 of the culture base 10 is brought into contact with the surface of the protruded part of the die 21b facing the die 21a. Next, the vessel 15 is forming being injection molded between the die 21a and 21b. In the die 21, the resin constituting the vessel 15 is introduced from a gate 21c. As a result, as shown in FIG. 6C, the vessel 15 including the culture base 10 can be formed. Regarding the resin used for injection molding, reference can be made to the description as to the material for forming the cell culture layer 13, for example. The resin may be the same as or different from the material for forming the cell culture layer 13.

When the culture base 10 is to be produced by a film forming method such as spin coating in the vessel 15 such as a dish, it is difficult to form the culture base 10 when the vessel 15 has a particular shape such as a circular shape. According to the method for producing the culture vessel 30 of the present embodiment, the photoresponsive layer 12 and the cell culture layer 13 are formed on the support layer 11, and the vessel 15 is formed for the obtained culture base 10. Therefore, the vessel 15 including the culture base 10 can be produced regardless of the shape of the vessel 15.

Next, another example of the method for producing the culture vessel 30 according to the third embodiment will be described with reference to FIGS. 7A to 7C.

Figure 7A:
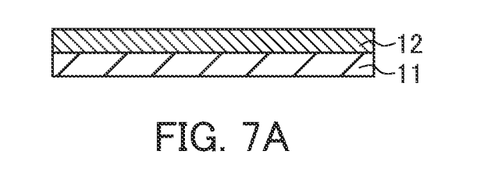
FIGS. 7A to 7C are schematic views showing another example of the method for producing a culture vessel according to the third embodiment.

In the method for producing the culture vessel 30 of the present embodiment, first, as shown in FIG. 7A, a member in which the photoresponsive layer 12 is laminated on the support layer 11 is produced. Specifically, in the method for producing the culture vessel 30, the photoresponsive layer 12 is laminated on the support layer 11 (first laminating step). The first laminating step is the same as that in the method for producing the culture base 10 of the first embodiment, and reference can be made to the description of the first embodiment.

Figure 7B:
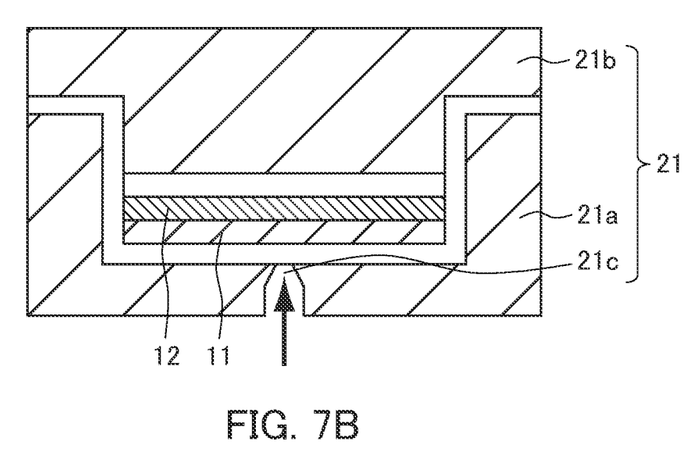
Figure 7C:
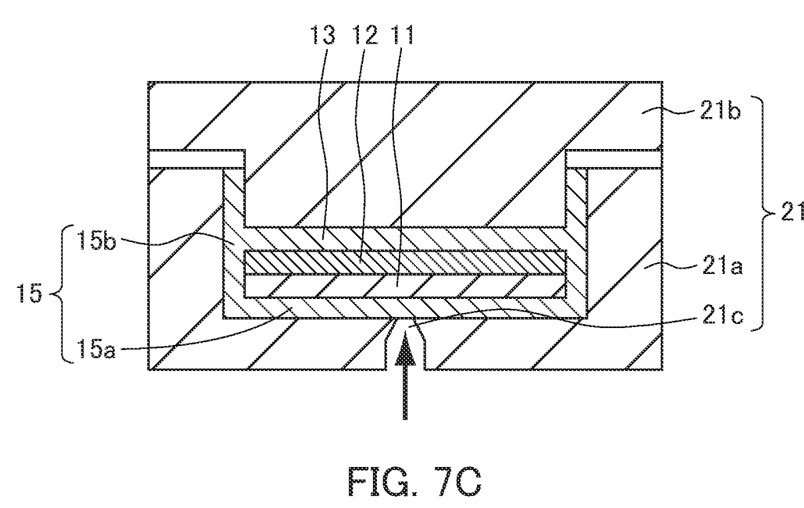

Next, as shown in FIGS. 7B and 7C, the vessel 15 including the support layer 11, the photoresponsive layer 12, and the cell culture layer 13 is formed (vessel forming step). In the vessel forming step, the cell culture layer 13 is formed at the same time as the vessel 15 is formed. Therefore, in the method for producing the culture vessel 30, the vessel forming step also serves as the second laminating step, that is, the second laminating step and the vessel forming step are performed simultaneously or in parallel.

First, a die 21 capable of forming the vessel 15 is prepared. The die 21 is composed of a die 21a (fixed side template) and a die 21b (working side template). As shown in FIG. 7B, between the surface of the protruded part of the die 21b facing the die 21a and the surface of the protruded part of the die 21a facing the die 21b, the aforementioned members are placed so as to be separated from the both surfaces of the die 21*a* and 21*b*. Next, the vessel 15 formed by injection molding between the die 21*a* and 21*b*. In the die 21, the resin constituting the vessel 15 is introduced from a gate 21*c*. As a result, as shown in FIG. 7C, since the vessel 15 is formed at the same time as the cell culture layer 13 is formed, the vessel 15 including the culture base 10 can be formed. According to the method for producing the culture vessel 30 of the present embodiment, the vessel 15 including the culture base 10 can be produced more easily.

While the method for producing the culture vessel 30 of the third embodiment was described with reference to the method for producing the culture vessel 30 using an injection molding, which is a film insert molding, as an example, the vessel forming step is not limited thereto. The vessel forming step may be performed, for example, by placing a culture base on the bottom surface of the cell culture area after forming the vessel 15.

The method for culturing the cells using the culture vessel 30 of the present embodiment can be performed, for example, in the same manner as that using the culture base 10 of the first embodiment described above.

In the culture vessel 30 of the third embodiment, since the cell culture layer 13 is laminated on the photoresponsive layer 12, the cell culture layer 13 is interposed between the cells cultured on the cell culture layer 13 and the photoresponsive layer 12. Thus, the culture vessel 30 of the third embodiment avoids contact between the photoresponsive layer 12 and the cells. Accordingly, for example, the influence on the cells can of the solvent used in formation of the photoresponsive layer 12, a side chain (e.g., the dye structure mentioned above) that is not bonded to the photo-thermal conversion polymer, or an unpolymerized monomer be prevented.

<Cell Culture Method>

The method for culturing cells of the present invention includes a culturing step of culturing cells using the cell culture base of the present invention, as described above. The culture method of the present invention is characterized in that the culture base of the present invention is used in the culturing step, and other steps and conditions are not particularly limited. Regarding the culture method of the present invention, reference can be made to the description as to the culture base and the culture vessel of the present invention.

The culture method of the present invention may use the culture vessel of the present invention as the culture base of the present invention.

The culture method of the present invention may include a selecting step of selecting a desired cell from the cells. Examples of the desired cell include undifferentiated stem cells of pluripotent cells such as embryonic stem cells (ES cells), iPS cells, and the like; and cells at a specific differentiation stage (differentiated cells). Examples of the differentiated cell include cardiac muscle cells, nerve cells, and liver cells. The culture method of the present invention may also include a step of controlling the position of the cells, i.e., a step of aligning the cells.

<Cell Production Method>

The method for producing cells of the present invention includes a culturing step of culturing cells using the cell culture base of the present invention, as described above. The production method of the present invention is characterized in that the culture base of the present invention is used in the culturing step, and other steps and conditions are not particularly limited. Regarding the cell production method of the present invention, reference can be made to the description as to the culture base, the culture vessel, and the culture method of the present invention.

The cell production method of the present invention may use the culture vessel of the present invention as the culture base of the present invention. The cell production method of the present invention may include a step of selecting a desired cell from the cells.

<Cell Culture Base Production Method>

The cell culture base production method of the present invention includes: a first laminating step of laminating a photoresponsive layer on a support layer; a second laminating step of laminating a cell culture layer on the photoresponsive layer, and wherein the photoresponsive layer contains a photoresponsive substance that causes at least one of heat and change in magnetism by light irradiation, and the cell culture layer is capable of culturing cells, as described above. The culture base production method of the present invention is characterized in that it includes the second laminating step, and other steps and conditions are not particularly limited. In the culture base production method of the present invention, since the cell culture layer is laminated on the photoresponsive layer, a culture base in which the cell culture layer is interposed between the cells cultured on the cell culture layer and the photoresponsive layer can be produced. Thus, the culture base obtained by the culture base production method of the present invention avoids contact between the photoresponsive layer and the cells. Accordingly, for example, the influence on the cells of the solvent used in formation of the photoresponsive layer, a side chain (e.g., the dye structure mentioned above) that is not bonded to the photo-thermal conversion polymer, or an unpolymerized monomer can be prevented. Regarding the culture base production method of the present invention, reference can be made to the description as to the culture base, culture vessel, and culture method of the present invention.

<Cell Culture Vessel Production Method>

The cell culture vessel production method of the present invention includes: a first laminating step of laminating a photoresponsive layer on a support layer; a second laminating step of laminating a cell culture layer on the photoresponsive layer; and a forming step of forming a vessel including the support layer, the photoresponsive layer, and the cell culture layer, wherein the photoresponsive layer contains a photoresponsive substance that causes at least one of heat and change in magnetism by light irradiation, and the cell culture layer is capable of culturing cells, as described above. The culture vessel production method of the present invention is characterized in that it includes the second laminating step, and other steps and conditions are not particularly limited. In the culture vessel production method of the present invention, since the cell culture layer is laminated on the photoresponsive layer, a culture vessel in which the cell culture layer is interposed between the cells cultured on the cell culture layer and the photoresponsive layer can be produced. Thus, the culture vessel obtained by the culture vessel production method of the present invention avoids contact between the photoresponsive layer and the cells. Accordingly, for example, the influence on the cells of the solvent used in formation of the photoresponsive layer, a side chain (e.g., the dye structure mentioned above) that is not bonded to the photo-thermal conversion polymer, or an unpolymerized monomer can be prevented. Regarding the culture vessel production method of the present invention, reference can be made to the description as to the culture base, culture vessel, and culture method of the present invention.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2019-085165 filed on Apr. 26, 2019. The entire subject matter of the Japanese Patent Application is incorporated herein by reference.

<Supplementary Notes>

Some or all of the above embodiments and examples may be described as the following supplementary notes, but are not limited thereto.

(Supplementary Note 1)

A cell culture base including: a support layer; a photoresponsive layer; and a cell culture layer, wherein the photoresponsive layer is laminated on the support layer, the cell culture layer is laminated on the photoresponsive layer, the photoresponsive layer contains a photoresponsive substance that causes at least one of heat and change in magnetism by light irradiation, and the cell culture layer is capable of culturing cells.

(Supplementary Note 2)

The cell culture base according to Supplementary Note 1, wherein the photoresponsive layer contains a photo-thermal conversion molecule that causes heat by light irradiation.

(Supplementary Note 3)

The cell culture base according to Supplementary Note 1 or 2, wherein the photoresponsive layer contains a magnetic substance that causes change in magnetism by light irradiation.

(Supplementary Note 4)

The cell culture base according to any one of Supplementary Notes 1 to 3, including a scaffold base layer, wherein the scaffold base layer contains a scaffold base, and the scaffold base layer is laminated on the cell culture layer.

(Supplementary Note 5)

The cell culture base according to any one of Supplementary Notes 1 to 4, wherein the support layer is a sheet-like support.

(Supplementary Note 6)

A cell culture vessel including: the cell culture base according to any one of Supplementary Notes 1 to 5.

(Supplementary Note 7)

A method for culturing cells, including: a culturing step of culturing cells using the cell culture base according to any one of Supplementary Notes 1 to 5.

(Supplementary Note 8)

The method according to Supplementary Note 7, wherein the cell culture base is a cell culture vessel including the cell culture base.

(Supplementary Note 9)

The method according to Supplementary Note 7 or 8, including: a selecting step of selecting a desired cell from the cells.

(Supplementary Note 10)

A method for producing cells, including: a culturing step of culturing cells using the cell culture base according to any one of Supplementary Notes 1 to 5.

(Supplementary Note 11)

A method for producing a cell culture base, including: a first laminating step of laminating a photoresponsive layer on a support layer; and a second laminating step of laminating a cell culture layer on the photoresponsive layer, wherein the photoresponsive layer contains a photoresponsive substance that causes at least one of heat and change in magnetism by light irradiation, and the cell culture layer is capable of culturing cells.

(Supplementary Note 12)

The method according to Supplementary Note 11, wherein the photoresponsive layer contains a photo-thermal conversion molecule that causes heat by light irradiation, and in the first laminating step, the photoresponsive layer is laminated using the photo-thermal conversion molecule.

(Supplementary Note 13)

The method according to Supplementary Note 11 or 12, wherein the photoresponsive layer contains a magnetic substance that causes change in magnetism, wherein in the first laminating step, the photoresponsive layer is laminated using the magnetic substance.

(Supplementary Note 14)

The method according to any one of Supplementary Notes 11 to 13, including a third laminating step of laminating a scaffold base layer on the cell culture layer, wherein the scaffold base layer contains a scaffold base.

(Supplementary Note 15)

A method for producing a cell culture vessel, including: a first laminating step of laminating a photoresponsive layer on a support layer; a second laminating step of laminating a cell culture layer on the photoresponsive layer; and a forming step of forming a vessel including the support layer, the photoresponsive layer, and the cell culture layer, wherein the photoresponsive layer contains a photoresponsive substance that causes at least one of heat and change in magnetism by light irradiation, and the cell culture layer is capable of culturing cells.

(Supplementary Note 16)

The method according to Supplementary Note 15, wherein the second laminating step and the forming step are performed simultaneously.

(Supplementary Note 17)

The method according to Supplementary Note 15 or 16, wherein the photoresponsive layer contains a photo-thermal conversion molecule that causes heat by light irradiation, and in the first laminating step, the photoresponsive layer is laminated using the photo-thermal conversion molecule.

(Supplementary Note 18)

The method according to any one of Supplementary Notes 15 to 17, wherein the photoresponsive layer contains a magnetic substance that causes change in magnetism, wherein in the first laminating step, the photoresponsive layer is laminated using the magnetic substance.

(Supplementary Note 19)

The method according to any one of Supplementary Notes 15 to 18, including a third laminating step of laminating a scaffold base layer on the cell culture layer, wherein the scaffold base layer contains a scaffold base.

INDUSTRIAL APPLICABILITY

As described above, in the culture base of the present invention, since the cell culture layer is laminated on the photoresponsive layer, the cell culture layer is interposed between the cells cultured on cell culture layer and the photoresponsive layer. Thus, the culture base of the present invention avoids contact between the photoresponsive layer and the cells. Accordingly, for example, the influence on the cells of the solvent used in formation of the photoresponsive layer, a side chain (e.g., dye structure described above) that is not bonded to the photo-thermal conversion polymer, or an unpolymerized monomer can be prevented. Therefore, the present invention is considerably useful in the field of life sciences, regenerative medicine, and the like in which cell culture is performed.

REFERENCE SIGNS LIST 10, 20: culture base
11: support layer
12: photoresponsive layer
13: cell culture layer
14: scaffold base layer
15: vessel
15a: bottom surface
15b: side wall
21, 21a, 21b: molding die
21c: gate
30: culture vessel

The invention claimed is:

1. A cell culture vessel comprising:
a photoresponsive layer; and
a blocking layer, wherein
the photoresponsive layer is placed in the cell culture vessel,
the blocking layer is laminated on the photoresponsive layer,
the photoresponsive layer contains a photoresponsive substance that causes at least one of heat and change in magnetism by light irradiation,
the blocking layer is capable of culturing cells and blocks the cells from contacting the photoresponsive layer,
in the cell culture vessel, a bottom surface of the cell culture vessel, the photoresponsive layer, and the blocking layer are laminated in an order in which the blocking layer is laminated over the photoresponsive layer and the photoresponsive layer is laminated over the bottom surface of the cell culture vessel,
wherein the blocking layer forms a bottom surface of a cell culture area in which cells can be cultured on an upper surface of the blocking layer and blocks the cells from contacting the photoresponsive layer, and
wherein a top surface of the photoresponsive layer in completely covered by a continuous layer of the blocking layer.

2. The cell culture vessel according to claim 1, wherein the photoresponsive layer contains a photo-thermal conversion molecule that causes heat by light irradiation.

3. The cell culture vessel according to claim 1, wherein the photoresponsive layer contains a magnetic substance that causes change in magnetism by light irradiation.

4. The cell culture vessel according to claim 1, comprising a support layer, wherein
the support layer is placed between the cell culture vessel and the photoresponsive layer.

5. The cell culture vessel according to claim 4, wherein the support layer is a sheet-like support.

6. The cell culture vessel according to claim 2, wherein the photo-thermal conversion molecule is a polymer containing a chromophore.

7. The cell culture vessel according to claim 6, wherein the polymer comprises a main chain and a side chain, wherein
the side chain comprises the chromophore.

8. The cell culture vessel according to claim 7, wherein the chromophore comprises a main chain and a side chain, wherein
the side chain comprises an azobenzene, a diarylethene, a spiropyran, a spirooxazine, a flugide, a leuco dye, an indigo, a carotenoid, a flavonoid, or quinoid.

9. A method for producing cells, comprising:
a culturing step of culturing cells using the cell culture vessel according to claim 1.

10. The method according to claim 9, comprising:
selecting a desired cell from the cultured cells.

11. A method for producing a cell culture vessel, comprising:
a first laminating step of laminating a photoresponsive layer on a support layer over at least a bottom surface of the cell culture vessel;
a second laminating step of laminating a blocking layer on the photoresponsive layer; and
a forming step of forming a vessel comprising the support layer, the photoresponsive layer, and the blocking layer, wherein
the photoresponsive layer contains a photoresponsive substance that causes at least one of heat and change in magnetism by light irradiation, and
the blocking layer is capable of culturing cells and blocks the cells from contacting the photoresponsive layer, and
wherein in the cell culture vessel, the bottom surface of the cell culture vessel, the photoresponsive layer, and the blocking layer are laminated in an order in which the blocking layer is laminated over the photoresponsive layer and the photoresponsive layer is laminated over the bottom surface of the cell culture layer,
wherein the blocking layer forms a bottom surface of a cell culture area in which cells can be cultured on an upper surface of the blocking layer and blocks the cells from contacting the photoresponsive layer, and
wherein a top surface of the photoresponsive layer is completely covered by a continuous layer of the blocking layer.

12. The method according to claim 11, wherein
the second laminating step and the forming step are performed simultaneously.

13. The method according to claim 11, wherein
the photoresponsive layer contains a photo-thermal conversion molecule that causes heat by light irradiation, and
in the first laminating step, the photoresponsive layer is laminated using the photo-thermal conversion molecule.

14. The method according to claim 11, wherein
the photoresponsive layer contains a magnetic substance that causes change in magnetism, wherein
in the first laminating step, the photoresponsive layer is laminated using the magnetic sub stance.

15. The cell culture vessel according to claim 1, wherein the blocking layer is formed integrally with the cell culture vessel or the blocking layer is a part of the cell culture vessel.

16. The cell culture vessel according to claim 1, wherein the photoresponsive layer and the bottom surface form a bottom side of the vessel.

* * * * *